(12) United States Patent
Maeda

(10) Patent No.: US 12,558,020 B2
(45) Date of Patent: Feb. 24, 2026

(54) MOTION SICKNESS ESTIMATION DEVICE, MOTION SICKNESS ESTIMATION METHOD, AND NON-TRANSITORY STORAGE MEDIUM

(71) Applicant: TOYOTA JIDOSHA KABUSHIKI KAISHA, Toyota (JP)

(72) Inventor: Shingo Maeda, Numazu (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 611 days.

(21) Appl. No.: 18/085,845

(22) Filed: Dec. 21, 2022

(65) Prior Publication Data

US 2023/0293086 A1 Sep. 21, 2023

(30) Foreign Application Priority Data

Mar. 17, 2022 (JP) ................................. 2022-042788

(51) Int. Cl.
*A61B 5/00* (2006.01)
*A61B 5/11* (2006.01)

(52) U.S. Cl.
CPC .......... *A61B 5/4023* (2013.01); *A61B 5/1103* (2013.01); *A61B 5/4842* (2013.01); *A61B 2503/12* (2013.01)

(58) Field of Classification Search
CPC ... A61B 5/4023; A61B 5/1103; A61B 5/4842; A61B 2503/12; A61B 5/163; A61B 5/6893
See application file for complete search history.

(56) References Cited

U.S. PATENT DOCUMENTS

| | | | | |
|---|---|---|---|---|
| 2012/0203309 A1* | 8/2012 | Englehart | .......... | A61N 1/36036 607/2 |
| 2015/0273179 A1* | 10/2015 | Krueger | ................ | G02C 11/00 600/27 |
| 2019/0022347 A1* | 1/2019 | Wan | .......................... | A61B 5/18 |
| 2019/0269321 A1* | 9/2019 | Murakami | ............ | A61M 21/00 |
| 2020/0269008 A1* | 8/2020 | Fabry | .................. | A61B 5/4023 |

(Continued)

FOREIGN PATENT DOCUMENTS

| | | |
|---|---|---|
| JP | 2020-131921 A | 8/2020 |
| WO | 2018/070330 A1 | 4/2018 |
| WO | 2021/111567 A1 | 6/2021 |

OTHER PUBLICATIONS

A. Brietzke, R. P. Xuan, A. Dettmann and A. C. Bullinger, "Concepts for Vestibular and Visual Stimulation to Mitigate Carsickness in Stop-and-Go-Driving," 2021 IEEE Intl Intelligent Transportation Systems Conference (ITSC), Indianapolis, IN, USA, 2021, pp. 3909-3916, doi: 10.1109/ITSC48978.202 (Year: 2021).*

(Continued)

*Primary Examiner* — Sun M Li
(74) *Attorney, Agent, or Firm* — Dinsmore & Shohl LLP

(57) ABSTRACT

The motion sickness estimation device includes an opening and closing detection unit configured to detect an opening/ closing state of an eye of a vehicle occupant, a face direction estimation unit configured to estimate an orientation of a face of the occupant, and an occupant state estimation unit configured to calculate a traveling speed of the motion sickness with respect to the occupant based on the opening/ closing state of the eye and the orientation of the face.

7 Claims, 8 Drawing Sheets

(56) References Cited

U.S. PATENT DOCUMENTS

| | | | |
|---|---|---|---|
| 2022/0001893 A1* | 1/2022 | Tartz | A61B 5/02055 |
| 2022/0001894 A1* | 1/2022 | Yeom | B60W 40/08 |
| 2023/0005279 A1* | 1/2023 | Shimizu | A61B 5/0077 |
| 2023/0143296 A1* | 5/2023 | Giovanardi | B60W 10/20 |
| | | | 701/37 |
| 2024/0362931 A1* | 10/2024 | Katz | G06V 40/20 |

OTHER PUBLICATIONS

L. Li, M. Xie and H. Dong, "A method of driving fatigue detection based on eye location," 2011 IEEE 3rd International Conference on Communication Software and Networks, Xi'an, China, 2011, pp. 480-484, doi: 10.1109/ICCSN.2011.6013949. (Year: 2011).*

Naoko Enami, Norimichi Ukita and Masatsugu Kidode, "Image matching robust to changes in imaging conditions with a car-mounted Camera," 2008 Second ACM/IEEE International Conference on Distributed Smart Cameras, Palo Alto, CA, USA, 2008, pp. 1-10, doi: 10.1109/ICDSC.2008.4635709. (Year: 2008).*

N. Ziraknejad, P. D. Lawrence and D. P. Romilly, "The effect of Time-of-Flight camera integration time on vehicle driver head pose tracking accuracy," 2012 IEEE International Conf on Vehicular Electronics and Safety (ICVES 2012), Istanbul, Turkey, 2012, pp. 247-254, doi: 10.1109/ICVES.2012.629429 (Year: 2012).*

\* cited by examiner

Figure 1:
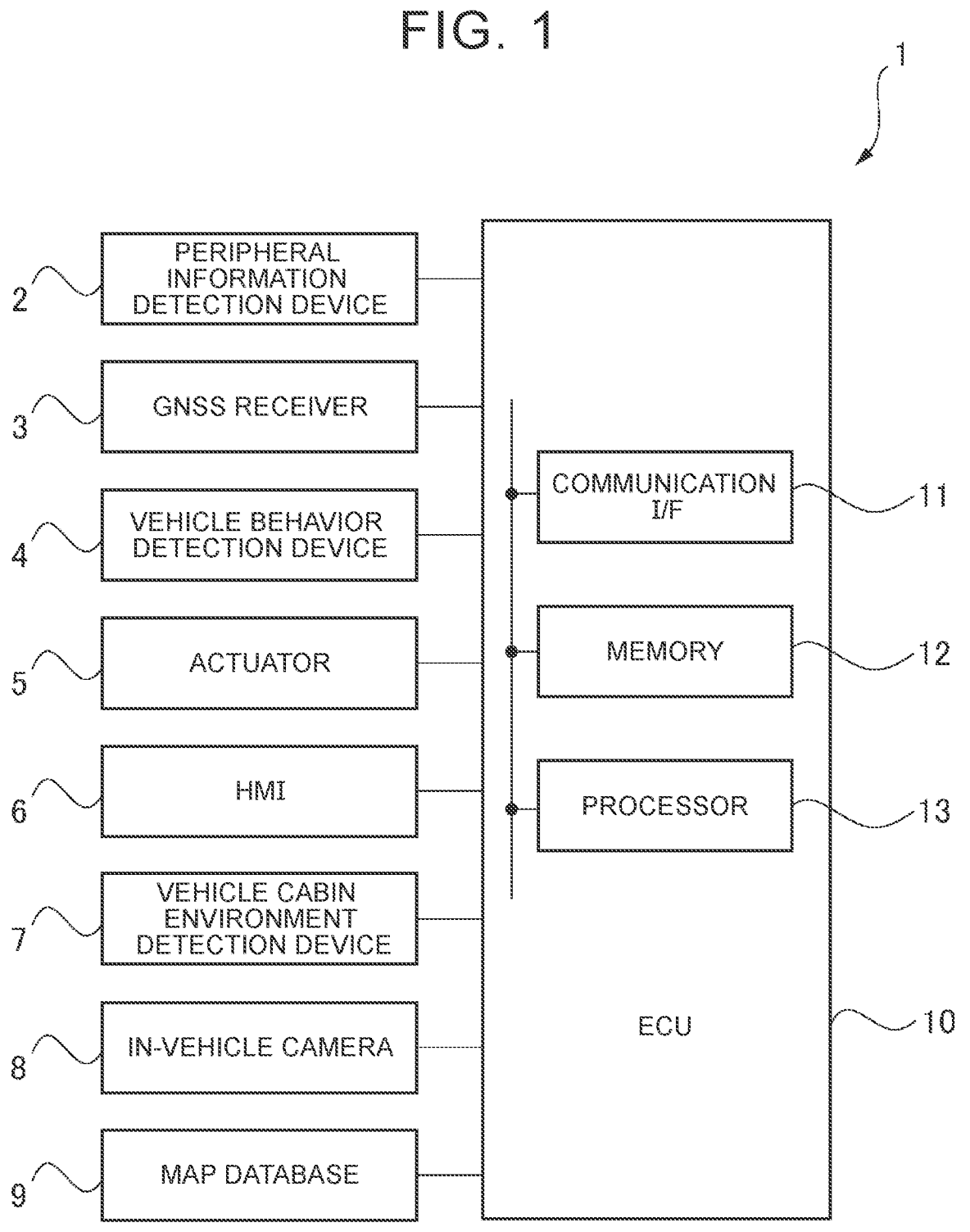

| | |
|---|---|
| 2 — PERIPHERAL INFORMATION DETECTION DEVICE | |
| 3 — GNSS RECEIVER | |
| 4 — VEHICLE BEHAVIOR DETECTION DEVICE | COMMUNICATION I/F — 11 |
| 5 — ACTUATOR | MEMORY — 12 |
| 6 — HMI | PROCESSOR — 13 |
| 7 — VEHICLE CABIN ENVIRONMENT DETECTION DEVICE | |
| 8 — IN-VEHICLE CAMERA | ECU — 10 |
| 9 — MAP DATABASE | |

FIG. 5

| PATTERN | OPENING AND CLOSING STATE OF EYE | DIRECTION OF FACE | GAIN |
|---|---|---|---|
| 1 | OPEN EYE | FRONT/SIDE | G1 |
| 2 | CLOSED EYE | FRONT/SIDE | G2 |
| 3 | CLOSED EYE | DOWN | G3 |
| 4 | OPEN EYE | DOWN | G4 |

FIG. 9

| PATTERN | OPENING AND CLOSING STATE OF EYE | DIRECTION OF FACE | MACHINE LEARNING MODEL |
|---------|----------------------------------|-------------------|------------------------|
| 1 | OPEN EYE | FRONT/SIDE | FIRST MODEL |
| 2 | CLOSED EYE | FRONT/SIDE | SECOND MODEL |
| 3 | CLOSED EYE | DOWN | THIRD MODEL |
| 4 | OPEN EYE | DOWN | FOURTH MODEL |

MOTION SICKNESS ESTIMATION DEVICE, MOTION SICKNESS ESTIMATION METHOD, AND NON-TRANSITORY STORAGE MEDIUM

CROSS-REFERENCE TO RELATED APPLICATION

This application claims priority to Japanese Patent Application No. 2022-042788 filed on Mar. 17, 2022, incorporated herein by reference in its entirety.

BACKGROUND

1. Technical Field

The present disclosure relates to a motion sickness estimation device, a motion sickness estimation method, and a non-transitory storage medium.

2. Description of Related Art

In a conveyance such as a vehicle, depending on the behavior of the conveyance, the state of an occupant, and the like, the occupant may suffer from motion sickness. WO 2018/070330 describes determining whether an occupant suffers from motion sickness based on a vibration difference between a vibration of a line of sight of the occupant and a vibration of an object located ahead of the line of sight.

SUMMARY

However, in a method for estimating motion sickness as described in WO 2018/070330, it is necessary to accurately detect the vibration of the line of sight and the vibration of the object, so that there is a possibility that sufficient estimation accuracy for motion sickness cannot be ensured.

In view of the above problems, an object of the present disclosure is to improve the estimation accuracy of the motion sickness.

The gist of the present disclosure is as follows.

A motion sickness estimation device according to a first aspect of the present disclosure includes: an opening and closing detection unit configured to detect an opening and closing state of an eye of an occupant of a conveyance; a face direction estimation unit configured to estimate a direction of a face of the occupant; and an occupant state estimation unit configured to calculate a progression rate of motion sickness of the occupant based the opening and closing state of the eye and the direction of the face.

In the motion sickness estimation device according to the first aspect, the occupant state estimation unit may be configured to calculate a reference value of the progression rate based on a first value indicating a behavior of the conveyance and a second value indicating a state of an internal environment of the conveyance, and to calculate the progression rate by correcting the reference value based on the opening and closing state of the eye and the direction of the face.

In the motion sickness estimation device according to the first aspect, the occupant state estimation unit may be configured to calculate a gain of the progression rate based on the opening and closing state of the eye and the direction of the face, and to calculate the progression rate by multiplying the reference value by the gain.

In the motion sickness estimation device according to the first aspect, the occupant state estimation unit may be configured to calculate the reference value by inputting the first value and the second value into a machine learning model.

In the motion sickness estimation device according to the first aspect, the occupant state estimation unit may be configured to increase the gain when the direction of the face is a downward direction as compared to when the direction of the face is a forward direction or a lateral direction.

In the motion sickness estimation device according to the first aspect, the occupant state estimation unit may be configured to increase the gain when the opening and closing state of the eye is in an open-eye state and the direction of the face is a downward direction as compared to when the opening and closing state of the eye is in a closed-eye state and the direction of the face is the downward direction.

In the motion sickness estimation device according to the first aspect, the occupant state estimation unit may be configured to increase the gain when the opening and closing state of the eye is in a closed-eye state and the direction of the face is a forward direction or a lateral direction as compared to when the opening and closing state of the eye is in an open-eye state and the direction of the face is the forward direction or the lateral direction.

In the motion sickness estimation device according to the first aspect, a plurality of machine learning models corresponding to different activity content of the occupant may be prepared in advance. Here, the occupant state estimation unit may be configured to select a calculation model from among the machine learning models based on the opening and closing state of the eye and the direction of the face, and to calculate the progression rate by inputting a first value indicating a behavior of the conveyance and a second value indicating a state of an internal environment of the conveyance into the calculation model.

A motion sickness estimation method according to a second aspect of the present disclosure is executed by a computer. The motion sickness estimation method is configured to include: detecting an opening and closing state of an eye of an occupant of a conveyance; estimating a direction of a face of the occupant; and calculating, based on the opening and closing state of the eye and the direction of the face, a progression rate of motion sickness of the occupant.

A non-transitory storage medium according to a third aspect of the present disclosure is a non-transitory storage medium storing instructions that are executable by one or more processors and that cause the one or more processors to perform functions including: detecting an opening and closing state of an eye of an occupant of a conveyance; estimating a direction of a face of the occupant; and calculating, based on the opening and closing state of the eye and the direction of the face, a progression rate of motion sickness of the occupant.

According to the present disclosure, it is possible to improve the estimation accuracy of the motion sickness.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 1 is a diagram schematically showing a configuration of a vehicle control system provided with a motion sickness estimation device according to a first embodiment of the present disclosure;

FIG. 5 is a diagram illustrating an example of a map for calculating a gain;

FIG. 9 is a diagram illustrating an example of a map for selecting a calculation model.

DETAILED DESCRIPTION OF EMBODIMENTS

Figure 2:
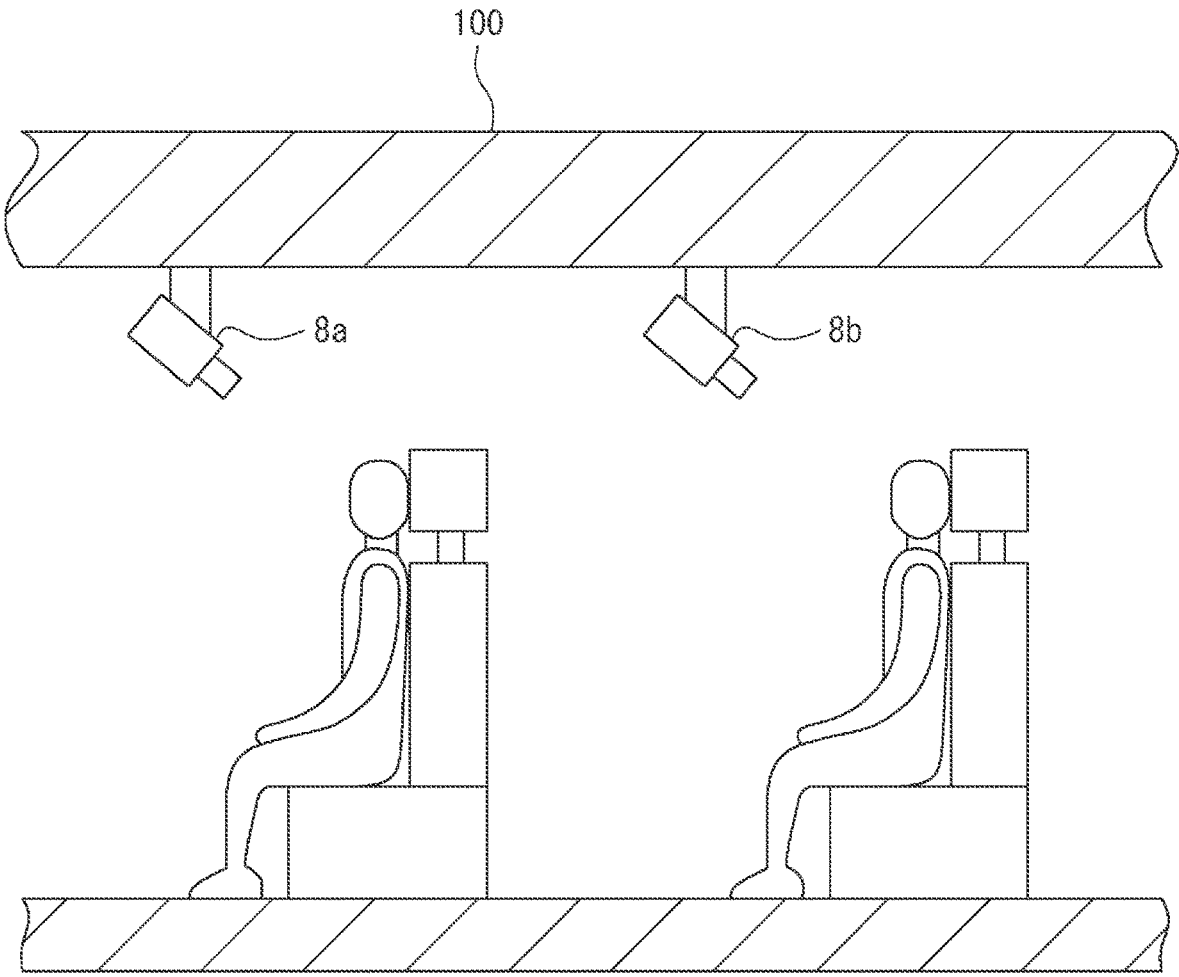
FIG. 2 is a diagram schematically showing the inside of a vehicle equipped with a vehicle control system.

Hereinafter, embodiments of the present disclosure will be described in detail with reference to the drawings. In the following description, similar components are given the same reference characters.

First Embodiment

Hereinafter, a first embodiment of the present disclosure will be described with reference to FIGS. 1 to 8. FIG. 1 is a diagram schematically showing a configuration of a vehicle control system 1 provided with a motion sickness estimation device according to a first embodiment of the present disclosure. As illustrated in FIG. 1, the vehicle includes a peripheral information detection device 2, a GNSS receiver 3, a vehicle behavior detection device 4, an actuator 5, an HMI 6, a vehicle cabin environment detection device 7, an in-vehicle camera 8, a map database 9, and an electronic control unit (ECU) 10. The peripheral information detection device 2, GNSS receiver 3, the vehicle behavior detection device 4, the actuator 5, HMI 6, the vehicle cabin environment detection device 7, the in-vehicle camera 8, and the map database 9 are electrically connected to ECU 10 via an in-vehicle network compliant with standards such as Controller Area Network (CAN).

The peripheral information detection device 2 acquires data (image data, point cloud data, and the like) around the vehicle, and detects peripheral information (for example, a peripheral vehicle, a pedestrian, a white line, and the like) of the vehicle. For example, the peripheral information detection device 2 may include a millimeter-wave radar, a camera (for example, a stereo camera), a Laser Imaging Detection And Ranging (LIDAR), or an ultrasonic sensor (sonar), or any combination thereof. The peripheral information detection device 2 outputs, that is, the peripheral information of the vehicles detected by the peripheral information detection device 2 is transmitted to ECU 10.

GNSS receiver 3 detects the present position of the vehicle (for example, the latitude and longitude of the vehicle) based on the positioning information obtained from a plurality of (for example, three or more) positioning satellites. Specifically, GNSS receiver 3 captures a plurality of positioning satellites and receives radio waves transmitted from the positioning satellites. Then, GNSS receiver 3 calculates the distance to the positioning satellite based on the difference between the transmission time and the reception time of the radio wave, and detects the present position of the vehicle based on the distance to the positioning satellite and the position (orbit information) of the positioning satellite. A specific example of GNSS receiver 3 is a GPS receiver. The power of GNSS receiver 3, i.e. the present position of the vehicles detected by GNSS receiver 3, is transmitted to ECU 10.

The vehicle behavior detection device 4 detects the behavior of the vehicle. The vehicle behavior detection device 4 includes, for example, a six-axis inertial sensor (IMU), a vehicle speed sensor, an acceleration sensor, an angular velocity sensor, and the like. The output of the vehicle behavior detection device 4, that is, the behavior of the vehicle detected by the vehicle behavior detection device 4 is transmitted to ECU 10.

The actuator 5 operates the vehicle. For example, the actuator 5 includes a drive device (for example, at least one of an internal combustion engine and an electric motor) for acceleration of the vehicle, a brake actuator for braking (decelerating) of the vehicle, and a steering actuator for steering of the vehicle. ECU 10 controls the actuator 5 to control the behavior of the vehicles. That is, the vehicle is an autonomous vehicle in which all of acceleration, steering, and deceleration (braking) of the vehicle are automatically executed, and ECU 10 performs autonomous travel of the vehicle using the actuator 5.

HMI 6 exchanges data between the vehicle and the occupant of the vehicle. HMI 6 includes an output unit (for example, a display, a speaker, a vibrating unit, and the like) for outputting information to an occupant of the vehicle, and an input unit (for example, a touch panel, an operation button, an operation switch, a microphone, and the like) for inputting information by the occupant of the vehicle. The power of ECU 10 is communicated to the occupant of the vehicle via HMI 6. In addition, an input from an occupant of the vehicle is transmitted to ECU 10 via HMI 6. HMI 6 may be an input device, an output device, or an input/output device. Note that a mobile terminal (smart phone, tablet terminal, etc.) of the occupant of the vehicle may be electrically connected to ECU 10 by wire or wirelessly, and may function as an HMI 6.

The vehicle cabin environment detection device 7 detects a state of an internal environment (cabin) of the vehicle. The vehicle cabin environment detection device 7 includes, for example, an oxygen sensor for detecting an oxygen concentration in the vehicle interior, a humidity sensor for detecting humidity in the vehicle interior, a temperature sensor for detecting a temperature in the vehicle interior, and the like. The output of the vehicle cabin environment detection device 7, that is, the state of the cabin detected by the cabin environment detection device 7 is transmitted to ECU 10.

The in-vehicle camera 8 is provided inside the vehicle so as to photograph an occupant of the vehicle, and generates an image of the occupant of the vehicle. The output of the in-vehicle camera 8, i.e. the images of the occupants of the vehicles generated by the in-vehicle camera 8, are transmitted to ECU 10.

FIG. 2 is a diagram schematically showing the inside of a vehicle 100 equipped with the vehicle control system 1. In the embodiment of FIG. 2, the vehicle 100 is provided with two rows of seats, and the in-vehicle camera 8 has a front camera 8a and a rear camera 8b. The front-camera 8a is arranged, for example, in a ceiling portion in front of the front row of seats and captures an image of an occupant of the front row of seats. The rear-camera 8b is disposed, for example, in a ceiling portion between the front row and the rear row, and captures an image of an occupant of a seat in the rear row. The front camera 8a and the rear camera 8b may be configured to simultaneously capture a plurality of occupants.

The map database 9 stores map information. ECU 10 obtains map data from the map database 9. Note that a map database may be provided outside the vehicle (e.g., servers, etc.), and ECU 10 may acquire map data from outside the vehicle by radio communication.

ECU 10 is configured as a computer and executes various types of control of vehicles. As shown in FIG. 1, ECU 10 includes a communication interface 11, a memory 12, and a processor 13. The communication interface 11 and the memory 12 are connected to the processor 13 via a signal line. In the present embodiment, one ECU 10 is provided, but a plurality of ECU may be provided for each function.

The communication interface 11 has interface circuitry for connecting ECU 10 to the in-vehicle networking. ECU 10 is connected to other in-vehicle devices via the communication interface 11. The communication interface 11 is an exemplary communication unit of ECU 10.

The memory 12 includes, for example, a volatile semiconductor memory and a non-volatile semiconductor memory. The memory 12 stores computer programs, data, and the like used when various kinds of processing are executed by the processor 13. The memories 12 are exemplary ECU 10 storage units.

The processor 13 comprises one or more Central Processing Unit (CPU) and its peripheral circuitry. The processor 13 may further include an arithmetic circuit such as a logical arithmetic unit or a numerical arithmetic unit.

In the autonomous driving vehicle as described above, since the traveling of the vehicle is automatically controlled, the occupant of the vehicle can freely perform an activity in the vehicle cabin. However, when the vehicle is traveling, an occupant of the vehicle may develop a motion sickness. Motion sickness, also referred to as agitation, is caused by a deviation between visual information obtained by the eye and a sense of equilibrium obtained by the semicircular canal. In an autonomous vehicle in which there is no driver for operating the vehicle, there is a possibility that the occupant's interest in the behavior of the vehicle is reduced and the motion sickness is accelerated. In order to suppress the onset of motion sickness, it is desirable to be able to accurately estimate the progress of motion sickness. Therefore, in the present embodiment, ECU 10 of the vehicle functions as a motion sickness estimation device, and estimates the motion sickness of the occupant.

Figure 3:
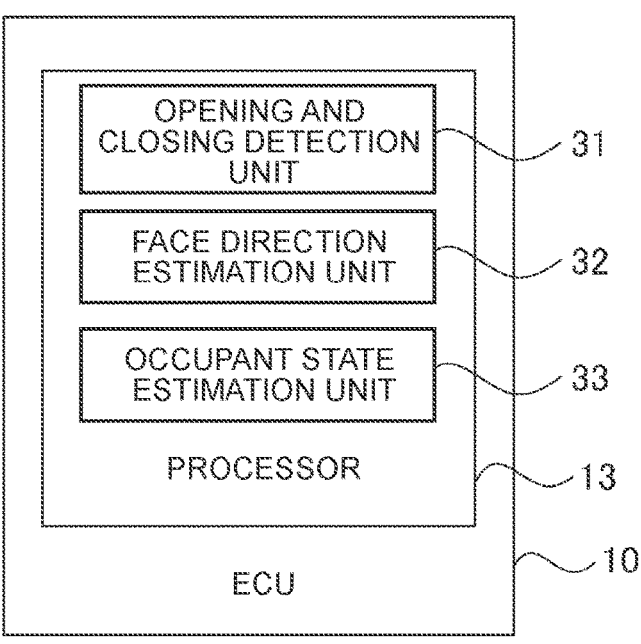
FIG. 3 is a functional diagram of a processor of an ECU.

FIG. 3 is a functional diagram of the processor 13 of ECU 10. In the present embodiment, the processor 13 includes an opening and closing detection unit 31, a face direction estimation unit 32, and an occupant state estimation unit 33. The opening and closing detection unit 31, the face direction estimation unit 32, and the occupant state estimation unit 33 are functional modules realized by ECU 10 processor 13 executing a computer program stored in ECU 10 memory 12. These functional modules may be realized by dedicated arithmetic circuits provided in the processor 13. In addition, these functional modules may be realized by a plurality of ECU connected to each other via an in-vehicle network. That is, a plurality of ECU may function as a motion sickness estimation device.

The opening and closing detection unit 31 detects an opening/closing state of an eye of an occupant of the vehicle (hereinafter, simply referred to as "occupant"). For example, the opening and closing detection unit 31 detects the opening/closing state of the eye of the occupant based on the image of the occupant generated by the in-vehicle camera 8. In this case, the opening and closing detection unit 31 identifies the face region of the occupant from the image of the occupant, and detects face components such as the eye, the nose, and the mouth. Then, the opening and closing detection unit 31 detects the degree of opening of the eye by extracting the feature points of the upper eyelid and the lower eyelid for each of the right eye and the left eye, and determines whether or not the occupant has opened the eye based on the degree of opening of the eye.

The opening and closing detection unit 31 may detect the opening/closing state of the eyes of the occupant by using an identifier learned in advance so as to output the opening/closing state (the opening state or the closing state) of the eyes of the occupant from the image of the occupant generated by the in-vehicle camera 8. Examples of such discriminators include machine learning models such as neural networks, support vector machines, random forests, and the like. Further, the opening and closing detection unit 31 may detect the opening/closing state of the eyes of the occupant on the basis of an output of a wearable terminal (for example, a glasses-type terminal) worn by the occupant. In this situation, for example, the wearable terminal is outputted to ECU 10 by radio communication.

The face direction estimation unit 32 estimates the direction of the face of the occupant. For example, the face direction estimation unit 32 estimates the direction of the face of the occupant based on the image of the occupant generated by the in-vehicle camera 8. In this case, the face direction estimation unit 32 calculates the angle of the face of the occupant from the image of the occupant, and estimates the direction of the face of the occupant based on the angle of the face.

The angle of the face of the occupant is calculated by, for example, the following method. The face shape data corresponding to the face facing the front is stored in advance, and the face direction estimation unit 32 performs matching between the face shape data and the face region of the image of the occupant. Then, the face direction estimation unit 32 rotates the face region of the image so that the coincidence rate between the face shape data and the face region of the image becomes maximum, and calculates the rotation angle when the coincidence rate becomes maximum as the angle of the face of the occupant. The face shape data may be data of an average face of a human being or data of a face acquired in advance for each occupant.

For example, the face direction estimation unit 32 calculates the yaw angle and the pitch angle of the face as the angle of the face. The yaw angle of the face is calculated as a positive value when the occupant is directed to the right, and is calculated as a negative value when the occupant is directed to the left. On the other hand, the pitch angle of the face is calculated as a positive value when the occupant faces upward, and is calculated as a negative value when the occupant faces downward. In the present embodiment, the face direction estimation unit 32 determines that the face direction of the occupant is downward when the pitch angle of the face is equal to or less than a predetermined value (for example, −10 degrees to −30 degrees), and determines that the face direction of the occupant is forward or sideways when the pitch angle of the face is larger than the predetermined value.

The face direction estimation unit 32 may detect a face region and a face component (mouth, nose, and both eyes)

of the occupant from an image of the occupant, and calculate an angle of the face of the occupant from a positional relationship between the face region and the face component. In addition, the face direction estimation unit 32 may estimate the direction of the face of the occupant by using an identifier learned in advance so as to output the direction (for example, forward direction, sideways direction, or downward direction) of the face of the occupant from the image of the occupant generated by the in-vehicle camera 8. Examples of such discriminators include machine learning models such as neural networks, support vector machines, random forests, and the like. In addition, the face direction estimation unit 32 may estimate the direction of the face of the occupant based on the output of the wearable terminal (e.g., glasses-type terminal) worn by the occupant. In this situation, for example, the wearable terminal is outputted to ECU 10 by radio communication.

The occupant state estimation unit 33 estimates the state of the occupant regarding the motion sickness. Specifically, the occupant state estimation unit 33 calculates the traveling speed of the motion sickness with respect to the occupant, and calculates the sickness level of the occupant by time-integrating the traveling speed of the motion sickness. Note that the sickness level is an index indicating the intensity of the symptom of the motion sickness, and the stronger the symptom of the motion sickness, the higher the sickness level.

As described above, motion sickness is caused by a deviation between visual information and a sense of balance. That is, when the vehicle is traveling, when the occupant of the vehicle cannot estimate the behavior of the vehicle from the visual information, the vehicle sickness is likely to occur. This sensory inconsistency is more pronounced when an occupant performs an operation (reading, operation of a portable terminal, etc.) independent of the behavior of the vehicle in the vehicle. Thus, the speed of travel of the motion sickness varies depending on the activity of the occupant in the vehicle. In addition, the activity content of the occupant in the vehicle can be estimated from the open/closed state and the face direction of the eyes of the occupant.

Therefore, the occupant state estimation unit 33 calculates the traveling speed of the vehicle sickness with respect to the occupant on the basis of the opening/closing state of the occupant's eye detected by the opening and closing detection unit 31 and the face direction of the occupant estimated by the face direction estimation unit 32. This makes it possible to reflect the activity of the occupant in the estimation of the progress of the motion sickness, and thus to improve the estimation accuracy of the motion sickness.

In addition, the traveling speed of the motion sickness is influenced by the behavior of the vehicle and the internal environment of the vehicle. For example, the motion sickness progresses when a gravitational acceleration (G) is applied to an occupant due to acceleration, deceleration, or turning of the vehicle, and the higher the value of the gravitational acceleration applied to the occupant, the faster the speed of the motion sickness progresses. In addition, when the oxygen concentration in the vehicle is low, the amount of oxygen taken into the body tends to be smaller and the speed of the motion sickness tends to be faster than when the oxygen concentration in the vehicle is high.

Therefore, in the present embodiment, the occupant state estimation unit 33 calculates the reference value of the traveling speed of the vehicle sickness based on the first value indicating the behavior of the vehicle and the second value indicating the state of the internal environment of the vehicle, and calculates the traveling speed of the vehicle sickness by correcting the reference value based on the opening/closing state of the eye of the occupant and the direction of the face. Specifically, the occupant state estimation unit 33 calculates a gain of the traveling speed of the motion sickness based on the opening/closing state of the eyes of the occupant and the direction of the face, and calculates the traveling speed of the motion sickness by multiplying the reference value by the gain.

Figure 4:
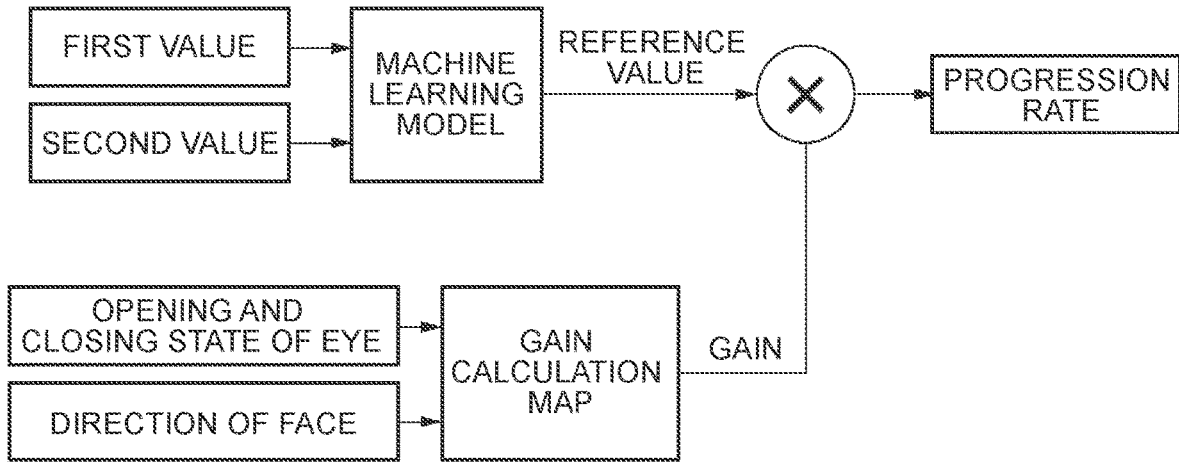
FIG. 4 is a diagram illustrating an algorithm for calculating a speed of travel of motion sickness.

FIG. 4 is a diagram illustrating an algorithm for calculating a traveling speed of motion sickness. As illustrated in FIG. 4, in the present embodiment, the occupant state estimation unit 33 calculates the reference value of the traveling speed of the motion sickness based on the first value and the second value using the machine learning model. Examples of such machine learning models include neural networks, support vector machines, random forests, and the like.

In the present embodiment, the first value indicating the behavior of the vehicle and the second value indicating the state of the internal environment of the vehicle correspond to the input parameter of the machine learning model, and the reference value of the traveling speed of the motion sickness corresponds to the output parameter of the machine learning model. The machine learning model is learned in advance using a large number of pieces of teacher data (training data), and the occupant state estimation unit 33 calculates a reference value by inputting the first value and the second value into the machine learning model.

Further, the occupant state estimation unit 33 calculates the gain of the traveling speed of the motion sickness based on the opening/closing state of the eyes of the occupant and the direction of the face. For example, the occupant state estimation unit 33 calculates a gain using a map (table) for gain calculation as illustrated in FIG. 5. In the example of FIG. 5, the activity content of the occupant is classified into four patterns based on the open/closed state of the eye of the occupant and the orientation of the face, and the gain value corresponding to each of the four patterns is set in advance. In the pattern 1, the gain value is set to G1, in the pattern 2, the gain value is set to G2, in the pattern 3, the gain value is set to G3, and in the pattern 4, the gain value is set to G4.

The pattern 1 corresponds to a state in which the open/closed state of the eye is the open-eye state and the face direction is the forward direction or the sideways direction. In the state of the pattern 1, it is highly likely that the occupant acquires information outside the vehicle as visual information, and it is considered that the degree of coincidence between the visual information and the behavior of the vehicle is high. The pattern 2 corresponds to a state in which the open/closed state of the eye is the closed-eye state and the face direction is the forward direction or the sideways direction. In the state of the pattern 2, the occupant does not have visual information, but since the direction of the face is along the traveling direction of the vehicle, it is considered that the occupant can predict the behavior of the vehicle to some extent. The pattern 3 corresponds to a state in which the open/closed state of the eye is the closed-eye state and the face is the downward direction. In the state of the pattern 3, since the occupant does not have visual information and the face direction does not follow the traveling direction of the vehicle, it is considered that it is difficult for the occupant to predict the behavior of the vehicle. The pattern 4 corresponds to a state in which the open/closed state of the eye is the open-eye state and the face is the downward direction. In the state of the pattern 4, there is a high possibility that the occupant performs work independent of the behavior of the vehicle, and it is considered that the deviation between the visual information and the behavior of the vehicle is large.

Therefore, the gain multiplied by the standard value output from the machine learning model is set to be larger in the order of Pattern 1, Pattern 2, Pattern 3, and Pattern 4 (G1<G2<G3<G4). That is, the occupant state estimation unit 33 increases the gain when the face is downward compared to when the face is forward or sideways (G1, G2<G3, G4). In addition, when the open/closed state of the eye is the open-eye state and the face is the downward direction, the occupant state estimation unit 33 increases the gain as compared with a case where the open/closed state of the eye is the closed-eye state and the face is the downward direction (G3<G4). In addition, when the open/closed state of the eye is in the closed eye state and the face is in the forward direction or the sideways direction, the occupant state estimation unit 33 increases the gain as compared with a case where the open/closed state of the eye is in the open eye state and the face is in the forward direction or the sideways direction (G1<G2).

The occupant state estimation unit 33 calculates the traveling speed of the motion sickness by multiplying the reference value output from the machine learning model by the gain calculated from the gain calculation map. The occupant state estimation unit 33 repeatedly calculates the travel speed of the motion sickness, and calculates the sickness level of the occupant by time-integrating the travel speed of the motion sickness.

Figure 6:
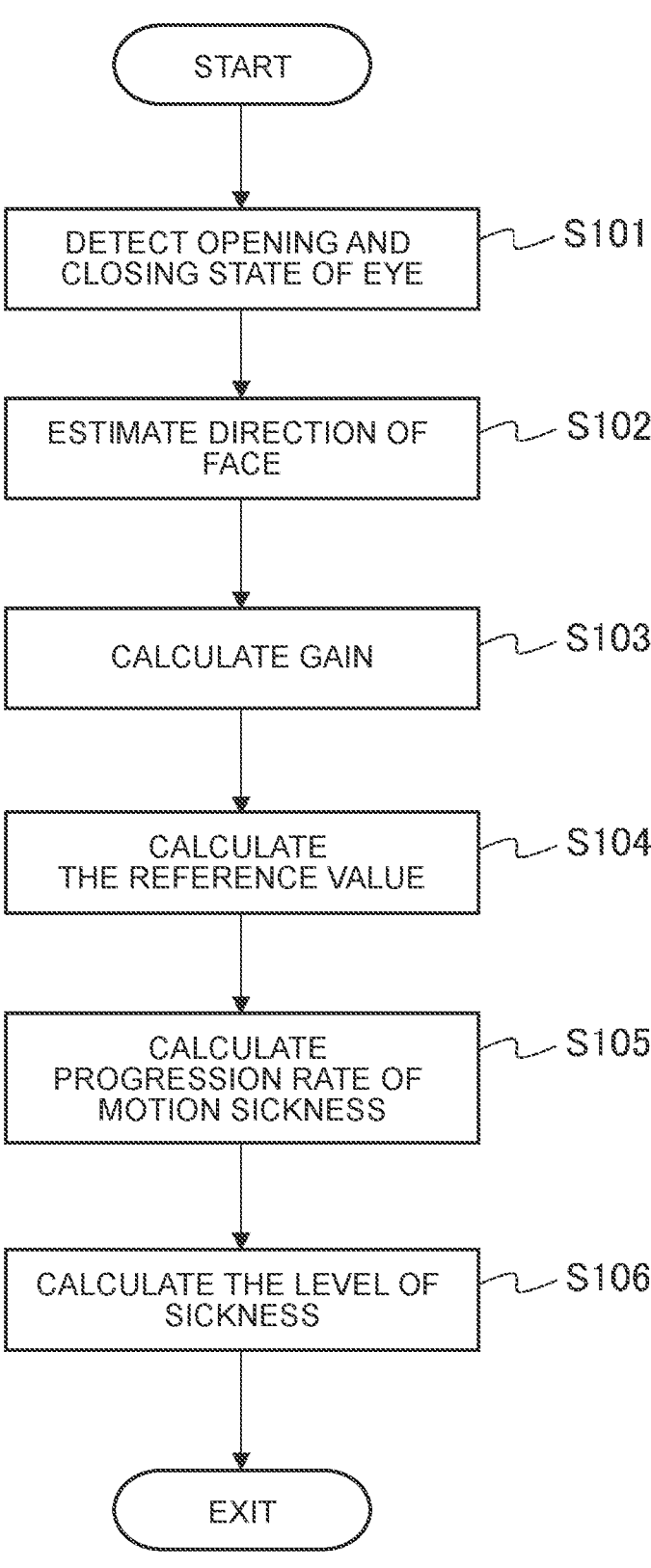
FIG. 6 is a flow chart illustrating a control routine performed to estimate a vehicle sickness of an occupant in a first embodiment.

Hereinafter, the flow of the above-described control will be described with reference to FIG. 6. FIG. 6 is a flowchart illustrating a control routine executed to estimate a motion sickness of an occupant in the first embodiment. The control routine is repeatedly executed by the processor 13 of ECU 10 at predetermined runtime intervals.

First, in S101 of steps, the opening and closing detection unit 31 detects the opening/closing condition of the eye of the occupant. After the step S101, in the step S102, the face direction estimation unit 32 estimates the orientation of the face of the occupant.

After S102 of steps, in the step S103, the occupant state estimation unit 33 calculates the gain of the traveling speed of the motion sickness based on the opening/closing state of the eyes of the occupant and the direction of the face. For example, the occupant state estimation unit 33 uses the gain calculation map as shown in FIG. 5 to identify the current occupant activity content based on the opening/closing state of the eye and the direction of the face, and acquires the gain value corresponding to the current occupant activity content. The gain value may be set for each occupant. In this case, for example, when the occupant is maintained in the state of the pattern 4, acceleration, deceleration, and turning of the vehicle are performed for a predetermined period of time, and a gain G4 is set based on a change in the sickness level reported by the occupant via HMI 6, and the gain G1 to G3 is calculated from the gain G4 by a predetermined calculation equation or the like.

After S103 of steps, in the step S104, the occupant state estimation unit 33 calculates a reference value of the traveling speed of the vehicle sickness based on the first value indicating the behavior of the vehicle and the second value indicating the state of the interior environment of the vehicle. For example, the output value of the vehicle behavior detection device 4 (for example, the output value of IMU) is used as the first value, and the output value of the vehicle cabin environment detection device 7 (for example, the output value of the oxygen sensor) is used as the second value. The occupant state estimation unit 33 calculates a reference value of the traveling speed of the motion sickness by inputting the first value and the second value into the machine learning model.

After S104 of steps, in the step S105, the occupant state estimation unit 33 calculates the traveling velocity of the motion sickness by multiplying the reference value by the gain. After S105 of steps, in the step S106, the occupant state estimation unit 33 calculates the occupant's sickness level by time-integrating the traveling velocity of the motion sickness. After S106 of steps, the control routine ends.

When there are a plurality of occupants in the vehicle, the sickness level is calculated for each of the plurality of occupants by the control routine of FIG. 6. When the sickness level of the at least one occupant reaches the predetermined threshold value, the occupant state estimation unit 33 may execute control for suppressing the sickness of the vehicle. For example, the occupant state estimation unit 33 reduces the upper limit value of the acceleration/deceleration of the vehicle, for example, as a control for suppressing the motion sickness. As a result, the vibration of the vehicle is reduced, and the motion sickness of the occupant can be suppressed. In addition, the occupant state estimation unit 33 may give a warning to the occupant via HMI 6 when the sickness level of the at least one occupant reaches a predetermined threshold. This may prompt the occupant to stop the act of promoting motion sickness.

Figure 7:
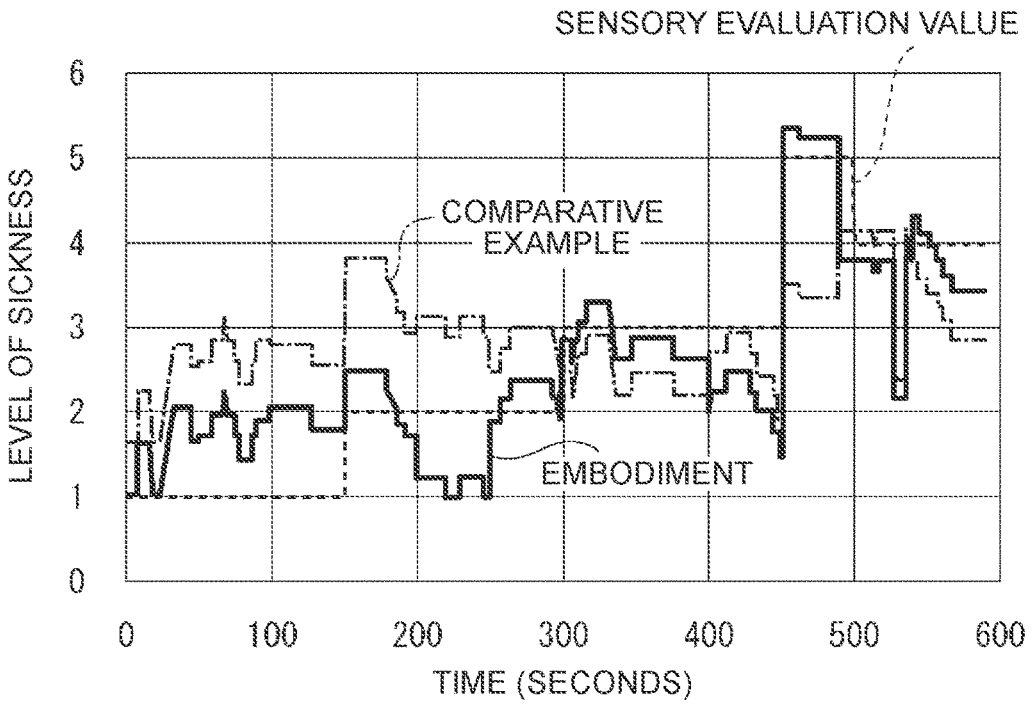
FIG. 7 is a diagram illustrating a difference between an estimation result of a sickness level according to an example and a comparative example and a sensory evaluation value of a sickness level according to a report by an occupant.
Figure 8:
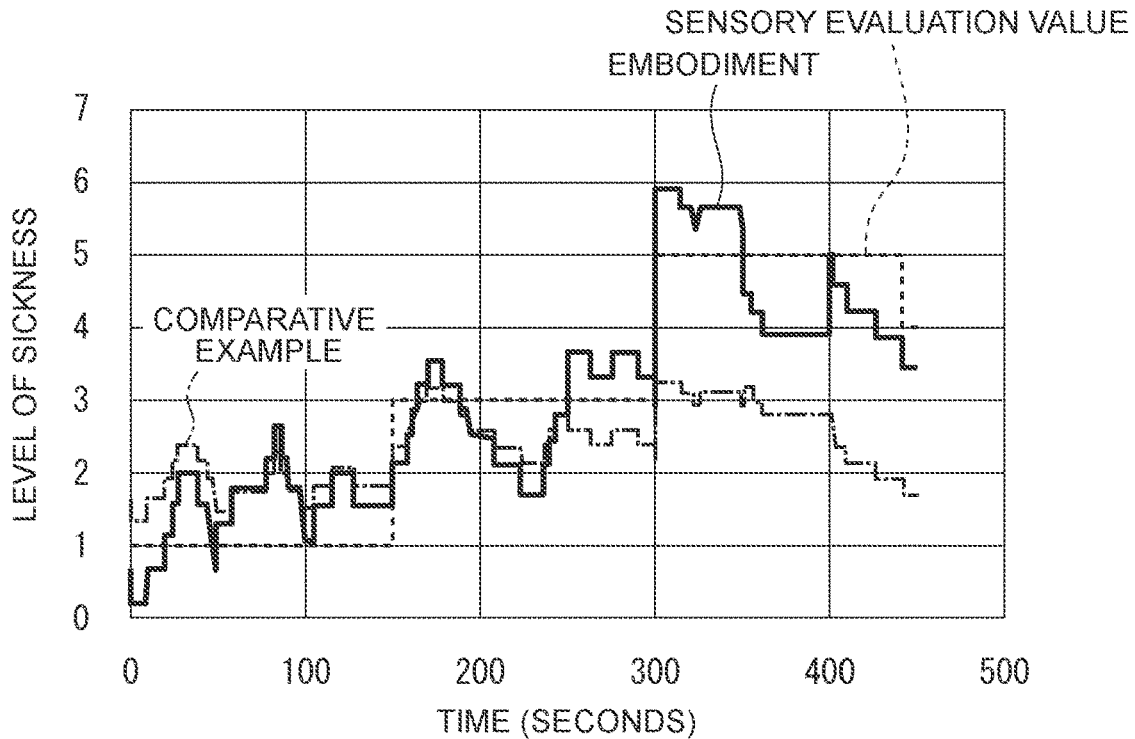
FIG. 8 is a diagram illustrating a difference between an estimation result of a sickness level according to an example and a comparative example and a sensory evaluation value of a sickness level according to a report by an occupant.

FIG. 7 and FIG. 8 are diagrams showing the difference between the estimation result of the sickness level according to the example and the comparative example and the sensory evaluation value of the sickness level according to the report by the occupant, respectively. In the states of the pattern 3 and the pattern 4, the motion sickness is accelerated and the fluctuation of the sickness level becomes remarkable as compared with the states of the pattern 1 and the pattern 2. For this reason, this experiment was carried out with the occupant kept in pattern 3 or pattern 4. FIG. 7 shows a result when the occupant is maintained in the state of the pattern 3 (a state in which the opening and closing state of the eye is a closed eye state and the face is a downward direction), and FIG. 8 shows a result when the occupant is maintained in the state of the pattern 4 (a state in which the opening and closing state of the eye is an open eye state and the face is a downward direction).

In FIG. 7 and FIG. 8, the estimation result according to the embodiment is indicated by a solid line, the estimation result according to the comparative example is indicated by a dashed-dotted line, and the sensory evaluation value is indicated by a dashed line. In the embodiment, the sickness level is calculated according to the control routine of FIG. 6, and in the comparative example, the sickness level is calculated using the conventional technique in which the activity content of the occupant is not reflected. In FIG. 7 and FIG. 8, a decrease in the level of sickness in Examples and Comparative Examples indicates that the vehicle has stopped.

In the result of FIG. 7, the interval average value of the squared error between the estimation result according to the comparative example and the sensory evaluation value was 1.36, and the interval average value of the squared error between the estimation result according to the example and the sensory evaluation value was 0.41. Therefore, in the example, it was confirmed that the motion sickness of the occupant in the state of the pattern 3 can be accurately estimated as compared with the comparative example.

In the result of FIG. 8, the interval average value of the squared error between the estimation result according to the comparative example and the sensory evaluation value was 2.10, and the interval average value of the squared error between the estimation result according to the example and the sensory evaluation value was 0.57. Therefore, in the example, it was confirmed that the motion sickness of the occupant in the state of the pattern 4 can be accurately estimated as compared with the comparative example.

Second Embodiment

The motion sickness estimation device according to the second embodiment is basically the same as the configuration and control of the motion sickness estimation apparatus according to the first embodiment except for the points described below. Therefore, the second embodiment of the present disclosure will be mainly described below with respect to portions different from the first embodiment.

In the first embodiment, the values of the plurality of gains corresponding to the different activities of the occupant are determined in advance, and the traveling speed of the motion sickness is calculated by switching the values of the gains according to the activities of the occupant. On the other hand, in the second embodiment, a plurality of machine learning models corresponding to different activity contents of the occupant are prepared in advance, and the progress speed of the motion sickness is calculated by switching the machine learning model according to the activity contents of the occupant. Each of the plurality of machine learning models has the same configuration as the machine learning model used for calculating the reference value in the first embodiment, and outputs the traveling speed of the motion sickness from the first value indicating the behavior of the vehicle and the second value indicating the state of the internal environment of the vehicle.

The occupant state estimation unit 33 selects a calculation model from among the plurality of machine learning models based on the opening/closing state of the eyes of the occupant and the direction of the face, and inputs the first value and the second value into the calculation model to calculate the traveling speed of the motion sickness. This makes it possible to reflect the activity of the occupant in the estimation of the progress of the motion sickness, and thus to improve the estimation accuracy of the motion sickness.

For example, the occupant state estimation unit 33 selects a calculation model using a model selection map (table) as illustrated in FIG. 9. In the example of FIG. 9, the activity content of the occupant is classified into four patterns based on the open/closed state of the eye of the occupant and the orientation of the face, and a machine learning model corresponding to each of the four patterns is prepared in advance. The state of patterns 1 to 4 shown in FIG. 9 is the same as the state of pattern 1 or r4 shown in FIG. 5. In the pattern 1, a first model is selected as a calculation model, in the pattern 2, a second model is selected as a calculation model, in the pattern 3, a third model is selected as a calculation model, and in the pattern 4, a fourth model is selected as a calculation model.

Each of the first model to the fourth model is learned in advance using a large number of pieces of teacher data (training data). At this time, different teacher data is used in the learning of the first model to the fourth model. The teacher data includes a combination of an input value (a first value and a second value) and an output value (a traveling speed of motion sickness), and the value of the output value used as the teacher data is set to be larger in the order of the first model, the second model, the third model, and the fourth model when the input values are the same (the first model<the second model<the third model<the fourth model). That is, the value of the traveling speed of the motion sickness output from the learned machine learning model basically increases in the order of the first model (pattern 1), the second model (pattern 2), the third model (pattern 3), and the fourth model (pattern 4).

Figure 10:
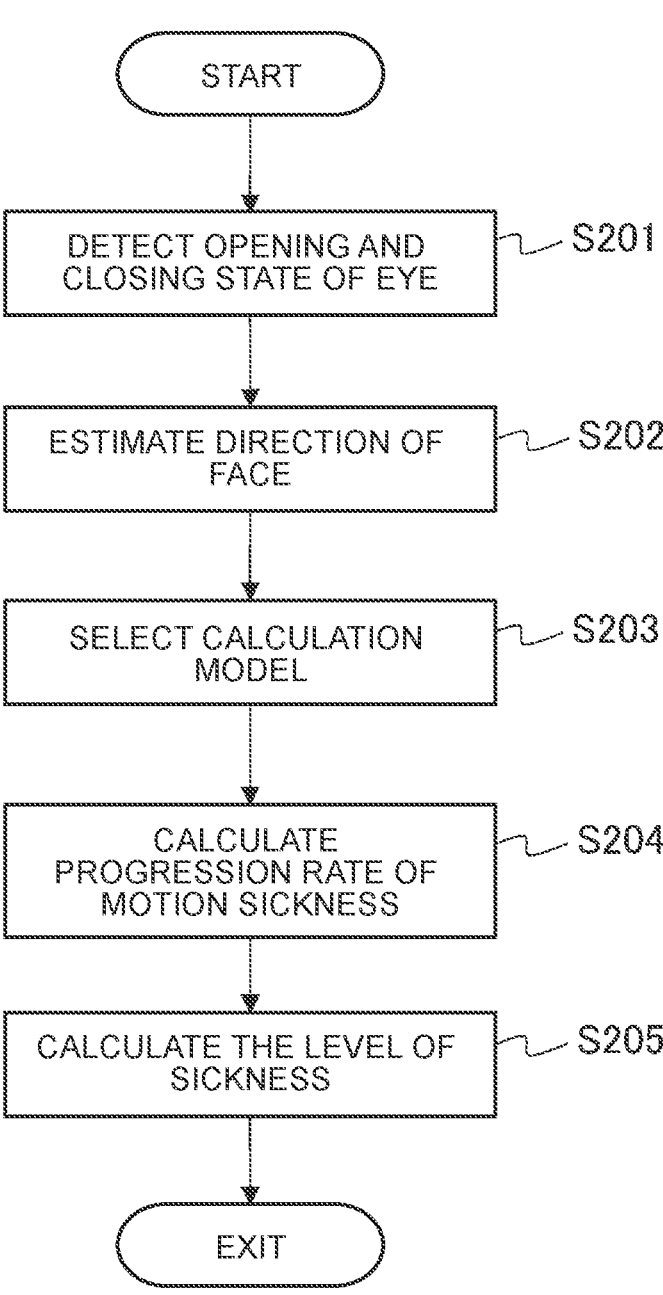
FIG. 10 is a flowchart illustrating a control routine executed to estimate a motion sickness of an occupant in the second embodiment.

FIG. 10 is a flowchart illustrating a control routine executed to estimate a motion sickness of an occupant in the second embodiment. The control routine is repeatedly executed by the processor 13 of ECU 10 at predetermined runtime intervals.

The steps S201 and S202 are performed similarly to the steps S101 and S102 of FIG. 6. After S202 of steps, in the step S203, the occupant state estimation unit 33 selects a calculation model from among the plurality of machine learning models based on the opening/closing state and the facial orientation of the eyes of the occupant. For example, the occupant state estimation unit 33 uses a model selection map as shown in FIG. 9 to identify the current occupant activity content based on the opening/closing state of the eye and the direction of the face, and selects a machine learning model corresponding to the current occupant activity content.

After S203 of steps, in the step S204, the occupant state estimation unit 33 calculates the traveling speed of the motion sickness based on the first value indicating the behavior of the vehicle and the second value indicating the state of the interior environment of the vehicle. For example, the output value of the vehicle behavior detection device 4 (for example, the output value of IMU) is used as the first value, and the output value of the vehicle cabin environment detection device 7 (for example, the output value of the oxygen sensor) is used as the second value. The occupant state estimation unit 33 calculates the traveling speed of the motion sickness by inputting the first value and the second value into the calculation model.

After S204 of steps, in the step S205, the occupant state estimation unit 33 calculates the occupant's sickness level by time-integrating the traveling velocity of the motion sickness. After S205 of steps, the control routine ends.

OTHER EMBODIMENTS

Although an embodiment of the present disclosure has been described above, the present disclosure is not limited to the embodiment, and various modifications can be made within the scope of the claims.

For example, the vehicle provided with the motion sickness estimation device may be a manual driving vehicle driven by a driver. In this case, the motion sickness for the occupant other than the driver is estimated by the motion sickness estimation device. Further, the motion sickness estimation device may be provided in a vehicle other than the vehicle (a ship, a train, an airplane, or the like). That is, the motion sickness estimation device may estimate the motion sickness for a vehicle occupant other than the vehicle.

Further, as the first value indicating the behavior of the vehicle, an output value or the like of the acceleration sensor attached to the occupant may be used. Here, for example, the power of the accelerometer is transmitted to ECU 10 by radio communication. Further, the vehicle cabin environment detection device 7 may include an odor sensor for detecting an odor in the vehicle cabin, and an output value of the odor sensor may be used as a second value indicating a state of the internal environment of the vehicle. Other parameters (e.g., passenger's temperature, heart rate, etc.) may also be used in addition to the first and second values or in place of the first and second values as input parameters to the machine learning model for outputting the reference value or the progress rate of motion sickness. In addition, the occupant state estimation unit 33 may calculate the reference value or the traveling speed of the motion sickness using a map or a calculation formula instead of the machine learning model.

Further, in the above-described embodiment, the activity content of the occupant is classified into four patterns based on the opening/closing state of the eyes of the occupant and the direction of the face, but the number of patterns may be other than four (for example, five or more). Further, the occupant state estimation unit 33 may calculate the traveling speed of the vehicle sickness with respect to the occupant by inputting the first value, the second value, the opening/ closing state of the occupant's eye, and the face direction of the occupant into the machine learning model. In this case, a value obtained by digitizing the opening/closing state and the face direction of the eye is input as an input parameter to the machine learning model.

In addition, a computer program that causes a computer to realize the functions of the respective units included in the processor of the motion sickness estimation device may be provided in a form stored in a computer-readable recording medium. The computer-readable recording medium is, for example, a magnetic recording medium, an optical recording medium, or a semiconductor memory.

What is claimed is:

1. A vehicle comprising:

a camera;

a memory; and a processor that is configured to:

acquire an image of an occupant from the camera, detect an opening and closing state of an eye of the occupant of the vehicle;

estimate a direction of a face of the occupant based on an angle of the face of the occupant calculated from the image of the occupant by performing matching between a face shape data stored in advance and a face region of the image of the occupant, maximizing a coincidence rate between the face shape data and the face region by rotating the face region of the image, and determining an rotation angle in the rotating the face region when the coincidence rate becomes maximum as the angle of the face;

calculate a gain of a progression rate of motion sickness of the occupant based on the opening and closing state of the eye and the direction of the face;

calculate a reference value of the progression rate based on a first value indicating a behavior of the vehicle and a second value indicating a state of an internal environment of the vehicle, calculate the progression rate by multiplying the reference value by the gain and by correcting the reference value based on the opening and closing state of the eye and the direction of the face, calculate a sickness level of the occupant based on the progression rate, execute control for suppressing motion sickness of the vehicle in response to the sickness level reaching a predetermined threshold including reducing an upper limit value of an acceleration or a deceleration of the vehicle, and increase the gain in a case that:

i) the opening and closing state of the eye is in an open-eye state and the direction of the face is a downward direction as compared to when the opening and closing state of the eye is in a closed-eye state and the direction of the face is the downward direction, or ii) the opening and closing state of the eye is in a closed-eye state and the direction of the face is a forward direction or a lateral direction as compared to when the opening and closing state of the eye is in an open-eye state and the direction of the face is the forward direction or the lateral direction.

2. The vehicle according to claim 1, wherein the processor is configured to calculate the reference value by inputting the first value and the second value into a machine learning model.

3. The vehicle according to claim 1, wherein a plurality of machine learning models corresponding to different activity content of the occupant is prepared in advance, and the processor is configured to select a calculation model from among the machine learning models based on the opening and closing state of the eye and the direction of the face, and to calculate the progression rate by inputting a first value indicating a behavior of the vehicle and a second value indicating a state of an internal environment of the vehicle into the calculation model.

4. The vehicle according to claim 1, wherein the opening and closing state of the eye of the occupant is detected based on an output of a wearable terminal worn by the occupant.

5. The vehicle according to claim 1, further comprising an oxygen sensor configured to detect an oxygen concentration in the vehicle, wherein the second value includes an output value of the oxygen sensor.

6. A motion sickness estimation method executed by a processor, the motion sickness estimation method comprising:

acquiring an image of an occupant from a camera;

detecting an opening and closing state of an eye of the occupant of a vehicle;

estimating a direction of a face of the occupant based on an angle of the face of the occupant calculated from the image of the occupant by performing matching between a face shape data stored in advance and a face region of the image of the occupant, maximizing a coincidence rate between the face shape data and the face region by rotating the face region of the image, and determining an rotation angle in the rotating the face region when the coincidence rate becomes maximum as the angle of the face;

calculating a gain of a progression rate of motion sickness of the occupant based on the opening and closing state of the eye and the direction of the face;

calculating a reference value of the progression rate based on a first value indicating a behavior of the vehicle and a second value indicating a state of an internal environment of the vehicle;

calculating the progression rate by multiplying the reference value by the gain and by correcting the reference value based on the opening and closing state of the eye and the direction of the face;

calculating a sickness level of the occupant based on the progression rate, executing control for suppressing motion sickness of the vehicle in response to the sickness level reaching a predetermined threshold including reducing an upper limit value of an acceleration or a deceleration of the vehicle, and increasing the gain in a case that:

i) the opening and closing state of the eye is in an open-eye state and the direction of the face is a downward direction as compared to when the opening and closing state of the eye is in a closed-eye state and the direction of the face is the downward direction, or ii) the opening and closing state of the eye is in a closed-eye state and the direction of the face is a forward direction or a lateral direction as compared to when the opening and closing state of the eye is in an open-eye state and the direction of the face is the forward direction or the lateral direction.

7. A non-transitory storage medium storing instructions that are executable by one or more processors and that cause the one or more processors to perform functions comprising:

acquiring an image of an occupant from a camera;

detecting an opening and closing state of an eye of the occupant of a vehicle;

estimating a direction of a face of the occupant based on an angle of the face of the occupant calculated from the image of the occupant by performing matching between a face shape data stored in advance and a face region of the image of the occupant, maximizing a coincidence rate between the face shape data and the face region by rotating the face region of the image, and determining an rotation angle in the rotating the face region when the coincidence rate becomes maximum as the angle of the face;

calculating a gain of a progression rate of motion sickness of the occupant based on the opening and closing state of the eye and the direction of the face;

calculating a reference value of the progression rate based on a first value indicating a behavior of the vehicle and a second value indicating a state of an internal environment of the vehicle;

calculating the progression rate by multiplying the reference value by the gain and by correcting the reference value based on the opening and closing state of the eye and the direction of the face;

calculating a sickness level of the occupant based on the progression rate, executing control for suppressing motion sickness of the vehicle in response to the sickness level reaching a predetermined threshold including reducing an upper limit value of an acceleration or a deceleration of the vehicle, and increasing the gain in a case that:

i) the opening and closing state of the eye is in an open-eye state and the direction of the face is a downward direction as compared to when the opening and closing state of the eye is in a closed-eye state and the direction of the face is the downward direction, or ii) the opening and closing state of the eye is in a closed-eye state and the direction of the face is a forward direction or a lateral direction as compared to when the opening and closing state of the eye is in an open-eye state and the direction of the face is the forward direction or the lateral direction.

* * * * *